United States Patent [19]

Bodmer et al.

[11] Patent Number: 5,098,823
[45] Date of Patent: Mar. 24, 1992

[54] CHROMOSOME-SPECIFIC NUCLEIC ACID PROBE FOR FAMILIAL POLYPOSIS COLI

[75] Inventors: Walter F. Bodmer; Victoria A. Murday; Carolyn J. Bailey; Robert Williamson, all of London, United Kingdom

[73] Assignee: Imperial Cancer Research Technology Ltd., London, United Kingdom

[21] Appl. No.: 460,896

[22] PCT Filed: Aug. 11, 1988

[86] PCT No.: PCT/GB88/00665
§ 371 Date: Apr. 12, 1990
§ 102(e) Date: Apr. 12, 1990

[87] PCT Pub. No.: WO89/01481
PCT Pub. Date: Feb. 23, 1989

[30] Foreign Application Priority Data

Aug. 12, 1987 [GB] United Kingdom ............... 8719061

[51] Int. Cl.⁵ ............... C12Q 1/68; C12N 1/20; G01N 33/566; C07H 15/12
[52] U.S. Cl. ............... 435/6; 435/252.3; 435/320.1; 436/501; 536/26; 536/27; 536/28; 935/77; 935/78
[58] Field of Search ............... 435/6, 253.3, 320; 436/501; 536/26, 27, 28; 935/77, 78

[56] References Cited

PUBLICATIONS

Nature, vol. 328, 13 Aug. 1987, W. F. Bodmer et al., pp. 614–616.
Nature, vol. 328, 13 Aug. 1987, E. Solomon et al., pp. 616–619.
Science, vol. 238, 4 Dec. 1987, M. Leppert et al., pp. 1411–1413.
Biological Abstracts/RRM, vol. 35, No. 64125, K. P. Meera et al. (Switzerland) 1987, vol. 46, No. 1–4, p. 661.
Biological Abstracts /RRM, vol. 35, No. 64065, M. Leppert et al. (Switzerland) 1987, vol. 46, No. 1–4, p. 647.
Genetic Analysis of Familial Polyposis Coli, Analysis of Gene Expression of Oncogenes in Colon Tumors of FPC by Kenji Sugio, Midical Inst. of Bioregulation, Kyushu University, Fukuoka 812, Japan, pp. 185–197.
The Gene for Familial Polyposis Coli Maps to the Long Arm of Chromosome 5, by M. Leppert et al., Science, vol. 238, No. 4832, pp. 1411–1413.

Primary Examiner—Robert A. Wax
Assistant Examiner—Stephanie W. Zitomer
Attorney, Agent, or Firm—Morrison & Foerster

[57] ABSTRACT

A nucleic acid fragment capable of selectively hybridizing with the human chromosome 5 at the chromosomal region 5q20-q23 is disclosed. Also disclosed are probes which include the fragment bearing a detectable level as well as processes for presymptomatic screening for FAP and processes for the pathological classification of colonic tumors and precancerous polyps.

21 Claims, 5 Drawing Sheets

CHROMOSOME-SPECIFIC NUCLEIC ACID PROBE FOR FAMILIAL POLYPOSIS COLI

TECHNICAL FIELD

The present invention relates to nucleic acid fragments and their use in the diagnosis and prognosis of adenocarcinoma especially Familial Adenomatous Polyposis.

BACKGROUND OF THE INVENTION

Colorectal cancer is the second most common cancer in the United Kingdom and other developed countries in the West. Although usually not familial there is a rare dominantly inherited susceptibility to colon cancer, Familial Adenomatous Polyposis (FAP or Familial Polyposis Coli). During adolescence affected individuals develop from a few hundred to over a thousand adenomatous polyps in their large bowel. These have a sufficiently high probability of giving rise to adenocarcinomas that prophylactic removal of the colon is recommended in diagnosed FAP individuals. Polyps may also occur elsewhere in the gastrointestinal tract and the condition is often associated with other extracolonic lesions, such as epidermoid cysts, jaw osteomata and fibrous desmoid tumours. [1,2,3,4]

Adenomata have been suggested to be precancerous states for the majority of colorectal tumours [5,6]. Knudson[7] has suggested that in both familial and non-familial cancers, dominant genes give rise to cancer susceptibility. He further proposed that these mutations act recessively at the cellular level, and that both copies of the gene must be lost for the cancer to develop. In sporadic cases both events occur somatically while in dominant familial cases susceptibility is inherited through a germ line mutation and the cancer develops following a somatic change in the homologous allele. This model was first substantiated by the elegant molecular work on retinoblastoma [2a]. Following the linkage of the disorder to chromosome 13[3a], Cavenee et al[2a], using polymorphic DNA markers for this chromosome, showed loss of heterozygosity in tumour material compared to normal tissue from the same patient, in both familial and non-familial forms. Similar results have now been obtained, following cytogenetic evidence which suggested the localisation of the disease on a specific chromosome, for Wilm's tumours [4a-7a], acoustic neuromas[8a] as well as several other tumours [9a,10a].

DISCLOSURE OF THE INVENTION

It has now been discovered that a DNA probe designated C11p11 localises to the chromosomal region 5q21-q22 and that this marker is closely linked to the disease gene for FAP. Moreover 20 to 25% of sporadic cases of adenocarcinoma of the colon involve changes in the human chromosome 5.

Accordingly the present invention provides a nucleic acid fragment capable of selectively hydridizing with the human chromosome 5 at the chromosomal region 5q20-q23.

In another embodiment, the present invention relates to a double stranded DNA fragment capable of selectively hybridizing under high stringency conditions with the human chromosome 5 at the chromosomal region 5q20-q23.

In other embodiments, the invention comprises processes for producing the subject fragments, nucleic acid probes comprising the fragments carrying a detectable label, processes for presymptomatic screening for FAP using these probes and processes for pathological classification of colonic tumors and precancerous polyps using the subject probes.

BRIEF DESCRIPTION OF THE FIGURES

Figure Legends

Methods

Blood samples were collected from family members and lymphocytes separated and frozen for future transformation with EBV[9]. High molecular weight DNA was extracted from both the residue of the separation and from the transformed lymphocytes. The cells were lysed in a solution containing 0.33M sucrose, 5 mM MgCl, 10 mM Tris-HCl pH 7.5, 1% Triton X-100. Nuclei were pelleted at 8000 g at 4° C. for 10 mins. and resuspended in 75 mM NaCl, 25 mM EDTA, 100 μg/ml Proteinase K and 0.5% SDS. The mixture was incubated overnight at 37° C. The aqueous phase was extracted 3 times in 2 mM Tris:2 mM EDTA buffered phenol and once in isoamyl alcohol/chloroform (1:24). The DNA was reprecipitated with 1/10 volume 3M sodium acetate pH 5.2 and two volumes absolute alcohol and then resuspended in TE. 10 μg aliquots of genomic DNA were digested overnight with 50 units of retriction enzyme, under the recommended conditions (Taq1 digests for 4-6 hours). The samples were run in 0.8% (w/v) agarose gels for 36-38 hours, at 1-1.5 V/cm. The gels were depurinated in 0.25M HCl for 10 mins, denatured in NaOH for 45 mins and then neutralized for 60 mins. The DNA was then transferred on to Hybond-N nylon filters (Amersham) by standard procedure[16].

Probes were labelled with [$\alpha^{32}$P]dCTP by the oligolabelling method[17] for 4-6 hours at 37° C. The filters were prehybridised in 6× SSC, 0.1% SDS, 5×Denhardts solution containing 25 μg/ml of denatured salmon sperm DNA for 1-2 hours at 65° C. Hybridisation was carried out overnight at 65° C. in the same solution but supplemented with 10 μCi/ml of labelled probe and 10% dextran sulphate.

L1.7 (D5S3[10]) is a 1.14 kb EcoRI fragment cloned into pBR322 and detects a BglII polymorphism with alleles A1 at 7.9 kb and A2 at 10.6 kb.

L1.7 also detects a PsTI polymorphism with alleles B1 at 2.8 kb and B2 at 2.3 kb.

L1.4 (D5S4[10]) is a 0.72 kb EcoRI fragment cloned into pBR322 and detects an EcoRI polymorphism producing alleles A1 at 0.7 kb and A2 a 0.6 kb.

L1.4 also detects an RsaI polymorphism with alleles C1 at 2.4 kb and C2 at 2.2 kb.

C11p11 is a 3.6 EcoRI fragment cloned into pUC8 and is polymorphic with TaqI producing alleles A1 at 3.9 kb and A2 at 4.4 kb.

λMS8[11] produces multiple alleles with HinfI.

HEXB[10] is a 1.5 kb XbaI fragment cloned into pSP64. A 1.1 kb BamHI/PstI fragment detects a PstI polymorphism with alleles A1 at 1.6 kb and A2 at 1.0 kb.

FIG. 2a

Representative chromosome spread showing in situ hybridisation of probe C11p11.

In situ hybridisation was performed on chromosomes prepared from PHA-stimulated normal blood lymphocytes essentially as described by Harper & Saunders[20]. The C11p11 probe was labelled using oligoprimers and $^3$H-deoxyribonucleotides to a specific activity of $1 \times 10^7$ cpm/μg/ml. Slides were washed in $2 \times$SSC at 39° C., dehydrated and dipped in Ilford K-5 emulsion. They were developed after 10 days.

Fine chromosome mapping was carried out with C11p11 probe, 221 silver grains were scored on chromosomes from 150 metaphases, with 22 grains (9.9%) present over bands 5q15-23 and the majority located over bands 5q21-22. Preliminary data for in situ hybridisation of the L1.4 probe localises it to band 5q31.

Localisation of λMS8 was done by in situ hybridisation by N. J. Royle and A. J. Jeffreys (unpublished data).

The symbols Δ regions represent the interstitial deletions reported by Herrera et al[8]

Figure Legends

FIG. 3—Chromosome 5 allele loss in primary colorectal tumours and cell lines

Methods

DNA was extracted from tumour biopsies (T) and normal adjacent mucosa (N) by standard methods[29]. For analysis with λMS8, DNA was digested with HinFI (New England Biolabs) and fractionated by agarose gel electrophoresis on 0.8% gels, for 60 hours at 20 mA; for L1.4 DNA was digested with EcoRI (Boehringer Corp. Ltd.), fractionated on 1.2% agarose gels, for 18 hours at 63 mA. In both cases DNA was transferred to Hybond-N Nylon membranes (Amersham) by standard procedures[30]. Probes were oligo-labelled[31] with $^{32}$P-CTP. Hybridisation and washing were by standard methods[29]. Patient numbers refer to Table 1.

FIG. 3b

Colorectal cell lines. DNA hybridised with λMS8. Methods are as in 1a. Cell lines are:

1) Coll2/23[32], 2) Coll 5/3[32], 3) HT29[33], 4) LoVo[34], 5) LS174T[35], 6) SV48[36], 7) SW620[36], 8) SW837[36], 9) SW1222[36], 10) PCJW[19], 11) PC/11[19]

Autoradiographs were scanned with a Joyce Loebl Chromocan 3. Areas under the peaks are plotted as the ratio of the two tumour alleles, $T_{P1}/T_2$, divided by the ratio of the two normal alleles $N_{P1}/N_2$. Those 7 cases which could be seen as clear allele loss are represented as ● (left to right: patients 9, 18, 19, 37, 17, 38, 35) and those with less obvious loss as o (patients 21 and 11).

DETAILED DESCRIPTION

The fragments of the invention may hybridise with the 5q20-q23 region under low or high stringency conditions and will be selective in that the fragments do not hydridise with other human chromosomal DNA under those conditions.

The nucleic acid fragments may be RNA or DNA but the latter is preferred. More preferably the fragment is double stranded DNA.

It is preferred that the present nucleic acid fragment will hybridize at the 5q21-q22 locus.

Nucleic acid fragments according to the invention may be obtained for instance by complete EcoRI digestion of human chromosome 5 (preferably after sorting the chromosomes, for instance by flow sorting), cloning in a suitable vector and amplification in a suitable host. Nucleic acid fragments according to the invention are then obtained by EcoRI digestion of the amplified vector and screening for hydridization to the 5q20-q23 region. This process has been used to prepare a 3.6 kb fragment which hybridises at the 5q21-q22 region and which recognises alleles of 3.9 and 4.4 kb in a TaqI digest of human chromosomes 5. The fragment forms a particular aspect of the present invention and has been designated C11p11.

Other nucleic acid fragments according to the invention include those which are capable of hydridizing to a C11p11 fragment although they may be longer or shorter than C11p11 provided that they still conform to the requirement for selective hybridisation of 5q20-q23. Such fragments may be produced by alternative digestions of human chromosome 5, by manipulation of C11p11 or a portion thereof or by de novo nucleic acid synthesis based on information obtained from sequencing for instance C11p11.

Further fragments according to the present invention are also capable of hydridising in the 5q20-q23 region but do not hybridise with the C11p11 fragment. These may be obtained for instance by alternative digestions of human chromosome 5 affording relatively long DNA fragments which will hybridize with C11p11 but which also include flanking sequences and, optionally after screening for C11p11 hybridisation and/or hybridisation at 5q20-q23, are further cut to obtain a flanking sequence which does not overlap with C11p11. This process may be repeated to obtain yet further fragments which still hybridise in the 5q20-q23 region but which represent flanking sequences more remote from the locus recognised by C11p11.

The invention also comprises a process for producing a fragment as hereinbefore defined comprising digesting human chromosomal DNA, cloning the library of fragments so obtained and screening and selecting fragments which hybridise selectively at the 5q20-q23 region of the chromosome.

For use as probes it is necessary for the fragments of the invention to be detectable after hydridisation with human DNA and this may be achieved by any known labelling technique. Typically the probe will be labelled by incorporation of radioisotopes (for instance by nick translation) which may be detected by autoradiography. Other labelling techniques include provision of directly detectable labels such as fluorescent labels and indirectly detectable labels such as enzyme labels. A skilled person will be aware of the techniques required for the introduction of these and other known labels and for the detection of such labels.

The invention therefore also provides a probe comprising a nucleic acid fragment as defined above having a detectable label attached thereto.

As discussed in more detail in the Examples, predisposition to FAP in afflicted families can be detected by heterozygosity in the 5q20-q23 region especially the 5q21-q23 region and the probes of the invention may be used to trace disease-related genes within families and to identify at-risk individuals.

Accordingly the invention provides a process for presymptomatic screening of an individual in an FAP family comprising contacting DNA from the individual with a probe of the invention under suitable hybridising conditions.

The process may be conducted as a pre- or post-natal screen to identify at-risk foetuses or individuals within FAP families and preferably further comprises screening relatives with and without FAP to identify and track a disease-related allele.

The invention also provides a process for pathological classification of colonic tumours and precancerous polyps comprising contacting DNA form a suspect tissue sample with a probe of the invention under suitable hybridising conditions. Identification of potential or actual tumours involving a 5q20-q23 abnormality may assist in prognosis and selection of appropriate treatment.

These processes may be conducted by standard methods such as by Southern blotting [30] using DNA from lymphocytes normal and/or tumour tissue obtained in blood samples or by biopsy. A general description of such restriction fragment length polymorphism (RFLP) analysis can be found in Scientific American, August 1987, pp21-22.

Further details of the invention will be apparent from the following Examples which are not intended to limit the scope of the invention in any way.

EXAMPLE 1

A case report of an interstitial deletion of chromosome 5 in a mentally retarded individual with multiple developmental abnormalities and FAP[8] promoted us to search for linkage of FAP to restriction fragment length polymorphisms (RFLPs) revealed by DNA clones assigned to chromosome 5. Our data show that the FAP gene is on chromosome 5, most probably near bands 5q21-22.

Figure 1:
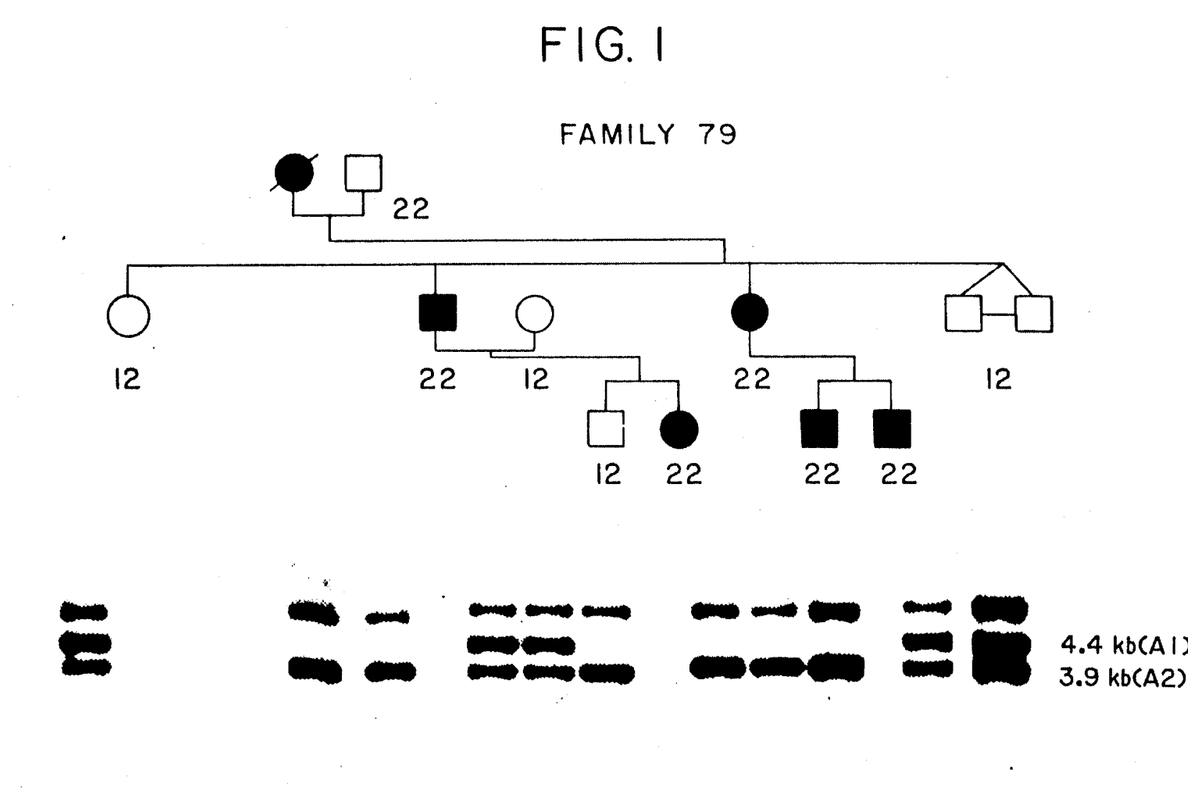
FIG. 1—Family 79 demonstrating segregation of FAP with a 3.9 Kb fragment using the probe C11p11.

Most of the families for the study were provided by the polyposis register at St. Marks Hospital, London and by The Gastroenterology Unit, Broadgreen Hospital, Liverpool and were well characterised with respect to clinical, pathological and pedigree information. Sterile blood samples were collected from these families and lymphocytes separated out and frozen. These were subsequently transformed by Epstein-Barr Virus (EBV) to produce a permanent source of DNA[9]. The sediment of these mononucleic cell separations was also used to provide an immediate source of DNA (legend FIG. 1.). Five polymorphic DNA probes assigned to chromosome 5 and mostly not regionally localised, were tested on up to 124 members from 13 different families. One of these, C11p11 (cloned by T. Robbins and kindly provided by R. Williamson) from flow sorted human chromosome sample by the method of T. C. Gilliam et al Human Genetics, 68, 154-158 (1984) showed evidence for close linkage to FAP. This probe is polymorphic with TagI, producing alleles at 3.9 kb and 4.4 kb with frequencies of about 0.92 and 0.08 (see FIG. 1). Six of the families, including 79 typed individuals, were informative and these gave a combined maximum lod score of 3.26 at a recombination fraction of 0=0. The lod scores for the linkage of FAP to L1.4[10] are also given and although not significant, give an estimate for the recombination fraction $\theta$, of about 0.1 (see Table O). The other probes (L1.7 from P. Pearson; $\lambda$MS8 from A. Jeffreys[11] and pHexXbaI from R. Gravel) showed no significant linkage with FAP or with each other. There was no obvious heterogeneity between the families with respect to the linkage of C11p11 with FAP. Assigning the most probable genotypes in all cases and assuming close linkage, the data are consistent with no recombinants amongst 24 meioses with no genotype predictions being necessary in 12 out of these 24 meioses.

Figure 2A:
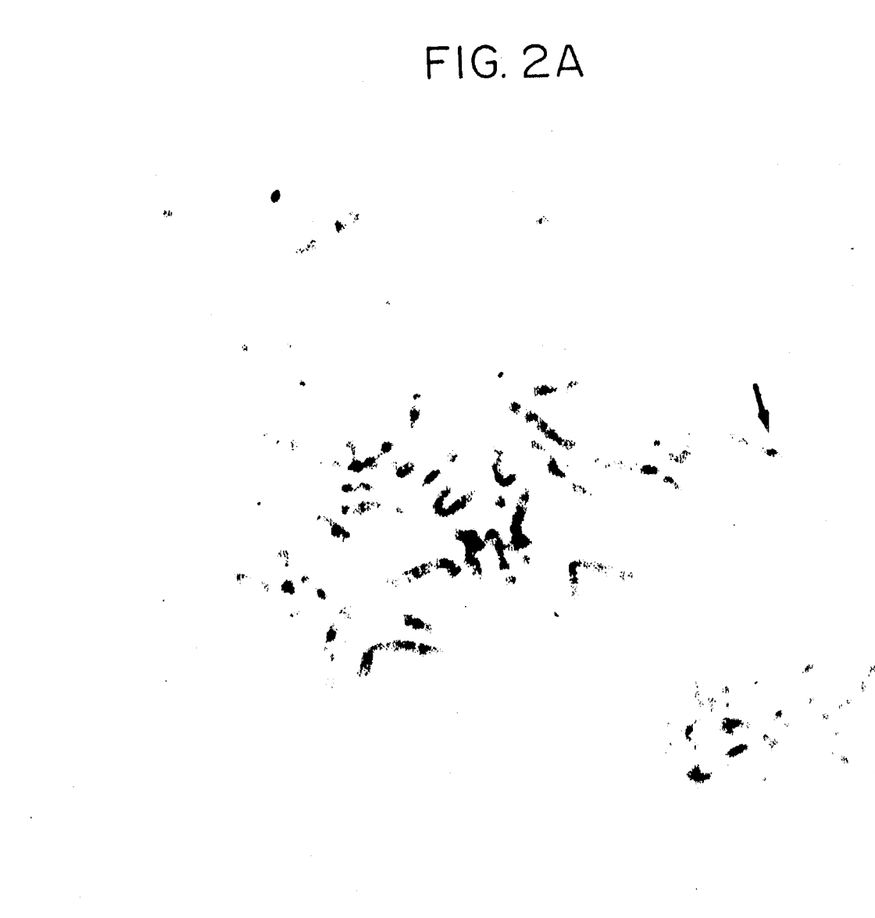
Figure 2B:
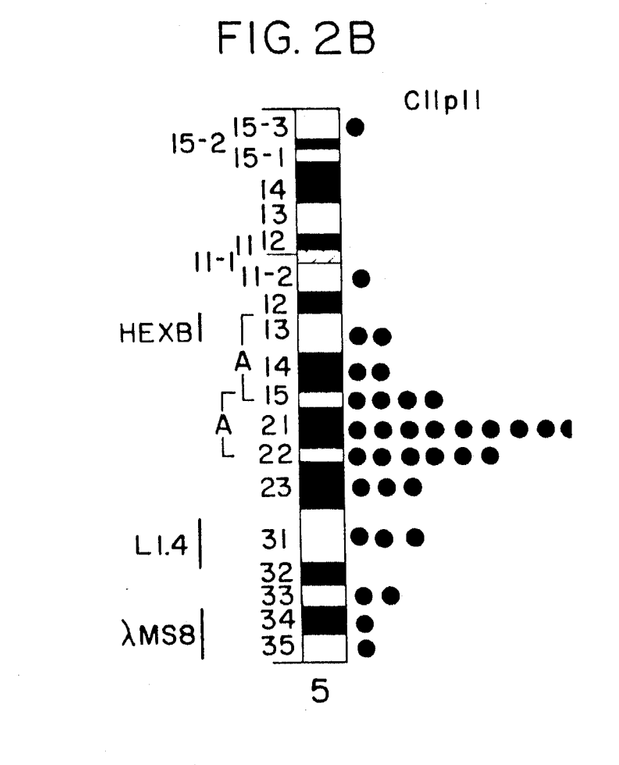
FIG. 2b—Fine chromosome mapping of probe C11p11 and putative regional assignment of probes L1.4 and λMS8.

In order to relate the linkage data to the interstitial deletion reported by Herrera et al.[8], in situ hybridisation was carried out to localise C11p11 and L1.4 on chromosome 5. Probe C11p11 localises to 5q21-22 (FIG. 2a) which is consistent with the deletion 5q15-22 of Herrera et al., rather than their cytogenetically indistinguishable alternative 5q13-15. This localisation is also consistent with a case report of a large bowel adenocarcinoma which has a 5q12!-22 deletion in addition to other cytogenetic abnormalities[12]. The lack of significant linkage between HEXB or $\lambda$MS8 and FAP is consistent with their localisations on the long arm of chromosome 5 (FIG. 2b). In the case of L1.4 this may be due to the small number of informative families rather than its localisation.

The demonstration in Example 2 that more than 20% of sporadic colorectal carcinomas become homo- or hemi-zygous for chromosome 5 alleles, the appreciable linkage with C11p11 and the coincidental localisation of the probe with the two deletions[8,12] provides overwhelming evidence for assignment of FAP to chromosome 5 probably to 5q21-22.

The marker loss data, together with the localisation of FAP, extend Knudson's ideas to FAP and, at least, a major subset of colorectal carcinomas. The data thus suggest that becoming recessive for a gene around 5q21-22 is a key step in the progression of many colorectal carcinomas, both sporadic and familial.

TABLE 0

| Lod scores from two point analyses for linkage between C11p11, L1.4 and FAP | | | | | |
|---|---|---|---|---|---|
| | Recombination fraction ($\theta$) | | | | |
| Marker loci | 0.0 | 0.10 | 0.20 | 0.30 | 0.40 |
| C11p11-FAP | 3.26 | 2.56 | 1.88 | 1.15 | 0.44 |
| L1.4-FAP | −2.50 | 0.78 | 0.66 | 0.37 | 0.12 |

The fact that polyps from FAP patients do not yet show the recessive change, as shown in the accompanying paper[13], is consistent with data using G6PD markers which suggested that polyps were not clonal[14].

One possibility of how heterozygosity for a deficiency can give rise to localised growth abnormalities such as the polyps is through a threshold effect involving, for example, negative control over the production of growth factors. In this model, the normal homozygote produces enough of the FAP gene product so that random fluctuations of its level do not, or at least only vary rarely, go below a threshold that permits localised excessive growth. The deficient heterozygote however, may allow random fluctuations in the production of FAP gene product relatively frequently enough for it to go below this threshold. In those localised areas of the colon where this happens, excessive epithelial growth may be initiated giving rise to polyps. Once initiated, this growth may persist by, for example, some form of feedback control for production of a growth factor. This is at least one way to explain how a gene dosage effect can give rise to discontinuous growths i.e. the polyps which look as though they should be clonal. Presumably the polyps, once they have arisen, provide the opportunity for the second, namely recessive, change to take place, followed no doubt by other changes which lead to the overt carcinoma.

The similarity in frequency of FAP throughout the world, together with the relatively high proportion of cases (up to 4%) which may be sporadic, namely new mutations[1], suggests that most FAP families may be different mutations. At the detailed genetic level the disease may therefore be quite hetergeneous. The incidence of FAP is estimated to be at least 1/10,000 and perhaps up to 1/5,000 which suggests that the mutation rate to FAP could be as high as 1/25,000. Perhaps there are sequences around the FAP gene which predispose to relatively high mutation rates by, for example, encouraging small deletions following unequal intrachromosomal double crossovers or gene conversion-like events.

Now that the FAP gene has been localised, long-range DNA analysis using pulsed field gel electrophoresis and chromosome jumping techniques[15], together with searches for appropriate epithelial specific messages coded for in this genetic region, should lead to the identification of the FAP gene and its function. This will not only provide a basis for the presymptomatic or prenatal diagnosis of FAP, but also lead to approached to counter-acting the FAP defect and may also provide new clues to specific treatments for at least some forms of sporadic colon carcinoma.

REFERENCES.DESCRIPTION AND EXAMPLE 1

1. Bulov, S. Danish Medical Bulletin. 34(1), 1-15 (1987).
2. Veale, A. M. O. Intestinal Polyposis, Cambridge. Cambridge University Press (1965).
3. Bussey, H. J. R. Familial polyposis coli. Baltimore. John Hopkins University Press, 1975.
4. Gardinar, E. Am. J. Hum. Genet. 3, 167-76 (1951).
5. Muto, T. et al 36(6), 2251-70 (1975).
6. Morson, B. C. Clinical Radiology 35, 425-31 (1984).
7. Knudson, A. G. Jnr. Proc. Natl. Acad. Sci. U.S.A. 68, 820-823 (1971).
8. Herrera, L. et al. Am. J. Med. Genet. 25, 473-476 (1986).
9. Miller & Lipman. Proc. Natl. Acad. Sci. U.S.A. 70, 190-194 (1973).
10. 8th Int. Workshop on Human Gene Mapping. Cyto. Cell Genet. 40(1-4), 1-824 (1985).
11. Wong Z. et al. Ann. Hum. Genet. 51, 269-288 (1987).
12. Ferti-Passantonopoulpu et al. Cancer Genetc. Cyto-genet 21, 361-4 (1986).
13. Solomon. F. et al, Nature 328, 618-619 (1987).
14. Hsu, S. H. et al. Science 221, 951-953 (1983).
15. Poustka, A. et al Nature 325, 353-355 (1987). Membrane transver and detection methods. Amersham (1985).
16. Stoker, N. Analytical Biochemistry 137, 266-267 (1984).
17. Smith, C. A. B. Am. J. Hum. Genet. 11(4), 289-304 (1959).
18. Ott, J. Am. J. Hum. Genet. 20, 588-597 (1974).

Example 2

The dominantly inherited disorder, Familial Adenomatous Polyposis (FAP or Familial Polyposis Coli), which gives rise to multiple adenomatous polyps in the colon that have a relatively high probability of progressing to a malignant adenocarcinoma[11] provides a basis for studying the role of recessive genes in the far more common colorectal carcinomas using this approach. Following a clue as to the location of the FAP gene given by a case report of an individual with an interstitial deletion of chromosome 5q, who had FAP and multiple developmental abnormalities[12], we have examined sporadic colorectal adinocarcinomas for loss of alleles on chromosome 5. Using a highly polymorphic "minisatellite" probe[13] which maps to chromosome 5q we have shown that at least 20% of this highly heterogeneous set of tumours loose one of the alleles present in matched normal tissue. This parallels the assignment of the FAP gene to chromosome 5 (see accompanying paper[14]) and suggests that becoming recessive for this gene may be a critical step in the progression of a relatively high proportion of colorectal cancers.

Figure 3A:
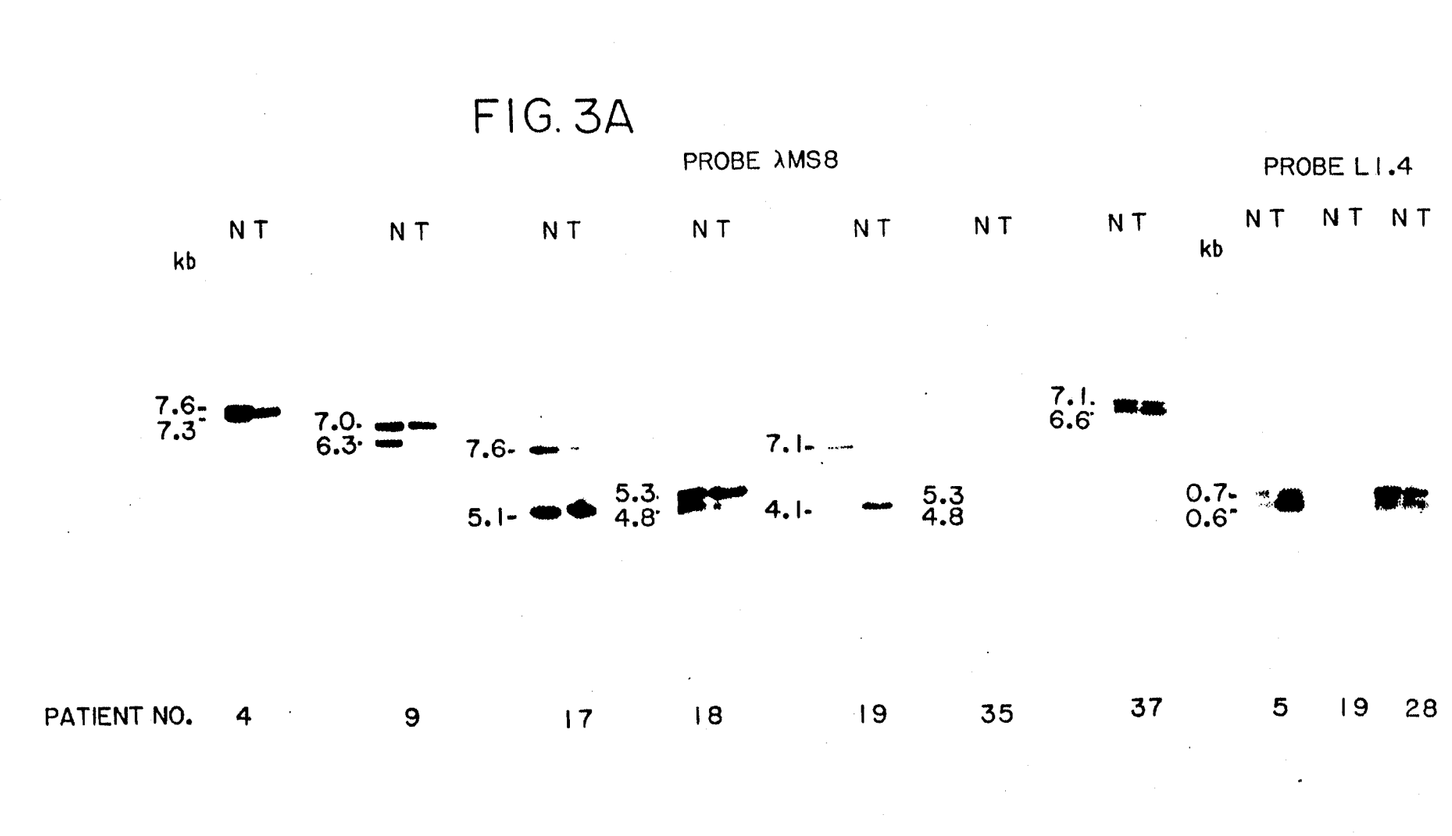
FIG. 3a—Primary colorectal tumours. DNA from matched normal/tumour pairs hybridised with λMS8 and L1.4

Tumour material and adjacent normal mucosa samples were collected from about 45 cases of colorectal carcinomas, mostly from St. Mark's Hospital, London. DNA preparations from these matched normal/tumour pairs were analysed from RFLP difference using a variety of probes that had been assigned to particular chromosomes. Following the clue that the FAP gene might be on chromosome 5, attention was concentrated on probe λMS8[13] which is a locus-specific mini-satellite probe that maps to chromosome 5q34-qter(N. J. Royle and A. J. Jeffrey, unpublished). Approximately 90% of individuals (55 out of 60 in our data) are heterozygous with this probe, showing two single band alleles with a Hinfl digests. This high level of heterozygosity makes it particularly valuable for these types of studies. Forty four heterozygous normal/tumour pairs were examined using Hinfl digests with this probe (Table 1A). Of these, seven tumours show clear alleles loss (nos. 9,17,18,19,35,37,38, for examples see FIG. 3A) and three others showed obvious, but less extreme changes in the ratio of one allele to the other when compared with normal tissue (nos. 4,11,21, FIG. 3A). These latter three cases are likely to be allele loss which is obscured by relatively large amounts of contaminating normal tissue in the tumour sample. Overall, 23% of tumours showed loss or alteration of an allele at this locus.

The same normal/tumour pairs were examined with a second probe, L1.4 which maps approximately to 5q31 (see Example 1) [14,15]. The RFLP allele frequencies detected with this probe, using ECoR1 are, on our data, 0.27 an d0.73. Seventeen informative pairs were studied and, of these, four showed clear allele loss (nos. 5,19,28,35, FIG. 3A) while two others showed an obvious change in the ratio of one allele to the other (nos. 9,11). Again, ambiguous results are probably due to contaminating normal tissue in the tumour sample. The overall results with this probe, namely 6 presumed losses out of 17, were similar to those with λMS8. There are not enough data to analyse any possible relationship between Dukes stage or tumour type or location and allele loss.

TABLE 1a

Allele losses in colorectal carcinomas with chromosome 5 probes λMS8 and L1.4

| PATIENT | TUMOUR TYPE | DUKES STAGING[20] | λMS8 Hinf I (no. alleles L1.4 detected) N | T | Eco R1 N | T |
|---|---|---|---|---|---|---|
| 1 | Ad. Ca. Rectum | C1 | 2 | 2 | 12 | 12 |
| 2 | Ad. Ca. Sigmoid Colon | B | 2 | 2 | 12 | |
| 3 | Ad. Ca. Rectum | C1 | 2 | 2 | | |
| 4 | Ad. Ca. Rectum | C1 | 2 | (1) | — | — |
| 5 | Ad. Ca. Rectum | C1 | — | — | 12 | 2 |
| 6 | Ad. Ca. Rectum | B | 2 | 2 | 12 | 12 |
| 7 | Ad. Ca. Rectum | C2 | 2 | 2 | | |
| 8 | Ad. Ca. Rectum | B | 2 | 2 | — | — |
| 9 | Ad. Ca. Sigmoid Colon | B | 2 | 1 | 12 | (2) |
| 10 | Ad. Ca. Rectum | A | 2 | 2 | — | — |
| 11 | Ad. Ca. Rectum | A | 2 | (1) | 12 | (1) |
| 12 | Ad. Ca. Sigmoid Colon | C1 | 2 | 2 | — | — |
| 13 | Ad. Ca. Rectum | C1 | 2 | 2 | 12 | |
| 14 | Ad. Ca. Rectum | B | 2 | 2 | — | — |
| 15 | Ad. Ca. Asc. Colon | B | 2 | 2 | 12 | 12 |
| 16 | Ad. Ca. Rectum | C1 | 2 | 2 | — | — |
| 17 | Mucinous Ad. Ca. Rectum | C1 | 2 | 1 | — | — |
| 18 | Ad. Ca. Rectum | B | 2 | 1 | — | — |
| 19 | Ad. Ca. Rectum | B | 2 | 1 | 12 | 2 |
| 20 | Ad. Ca. Rectum | C1 | 2 | 2 | — | — |
| 21 | Ad. Ca. Sigmoid Colon | B | 2 | (1) | 12 | 12 |
| 22 | Mucinous Ad. Ca. Asc. Colon | B | 2 | 2 | 12 | 12 |
| 23 | Ad. Ca. Rectum | B | 2 | 2 | — | — |
| 24 | Ad. Ca. Rectum | B | 2 | 2 | — | — |
| 25 | Ad. Ca. Sigmoid Colon | B | 2 | 2 | — | — |
| 26 | Ad. Ca. Rectum | C1 | 2 | 2 | — | — |
| 27 | Ad. Ca. Rectum | C1 | 2 | 2 | — | — |
| 28 | Ad. Ca. Rectum | A | 2 | 2 | 12 | 2 |
| 29 | Ad. Ca. Asc. Colon | C1 | 2 | 2 | — | — |
| 30 | Ad. Ca. Rectum | C1 | 2 | 2 | — | — |
| 31 | Mucinous Ad. Ca. Asc. Colon | B | 2 | 2 | — | — |
| 32 | Ad. Ca. Rectum | B | 2 | 2 | — | — |
| 33 | Ad. Ca. Rectum | C1 | 2 | 2 | — | — |
| 34 | Ad. Ca. Sigmoid Colon | B | 2 | 2 | — | — |
| 35 | Ad. Ca. Sigmoid Colon | B | 2 | 1 | 12 | 2 |
| 36 | Ad. Ca. Rectum | B | 2 | 2 | — | — |
| 37 | Ad. Ca. Sigmoid Colon | B | 2 | 1 | — | — |
| 38 | Ad. Ca. Sigmoid Colon | B | 2 | 1 | — | — |
| 39 | Ad. Ca. Rectum | C1 | 2 | 2 | 12 | 12 |
| 40 | Ad. Ca. Sigmoid Colon | C1 | 2 | 2 | 12 | 12 |
| 41 | Ad. Ca. Rectum | B | 2 | 2 | — | — |
| 42 | Ad. Ca. Desc. Colon | B | 2 | 2 | 12 | 12 |
| 43 | Ad. Ca. Desc. Colon | C | 2 | 2 | 12 | 12 |
| 44 | Ad. Ca. Rectum | B | | | 12 | 12 |
| 45 | Ad. Ca. Asc. Colon | B | 2 | 2 | 12 | 12 |

TABLE 1b

Combined λMS8 and L1.4 allele losses in cases where both probes are informative

| λMS8 no loss | L1.4 no loss | λMS8 no loss | L1.4 loss | λMS8 loss | L1.4 no loss | λMS8 loss | L1.4 loss | Total |
|---|---|---|---|---|---|---|---|---|
| 9 | | 1 | | 1 | | 4 | | 15 |

TABLE 1

Ad.Ca. - Adenocarcinoma; Asc. - ascending Desc. - descending. Tumour material and adjacent normal mucosa from colorectal cancer patients, obtained during surgery, was frozen immediately in liquid nitrogen. DNA was analysed by standard methods, see legend to FIG. 1. λMS8 detects alleles of different sizes in almost every individual so that each sample is indicated as having 2 or 1 alleles rather than particular allele sizes. The L1.4 alleles are 0.7 kb (allele 1) and 0.6 kb (allele 2). "-" indicates non-informative samples, due to lack of heterozygosity. A blank space indicates no information. Those tumour samples with less certain allele loss are shown with the most prominent remaining allele in parenthesis.

The results for cases in which both markers λMS8 and L1.4 were informative are summarised in Table 1B. A total of 6/15, or 40%, showed changes for one or other marker, although with such small numbers, this is not significantly higher than the 10/44 for λMS8 alone. Four out of six were changed for both markers, suggesting a high frequency of overall chromosomal loss. A more localised deletion or somatic recombination, would explain case number 28 with loss at L1.4 but not λMS8. One case, number 21, with loss at λMS8 but not L1.4 is inconsistent with these interpretations given the presumed map order centromere-FAP-L1.4-λMS8 (see accompanying paper). This could, once again, be the result of misclassification for one of the markers due to contaminating normal tissue in the tumour material.

Figure 4:
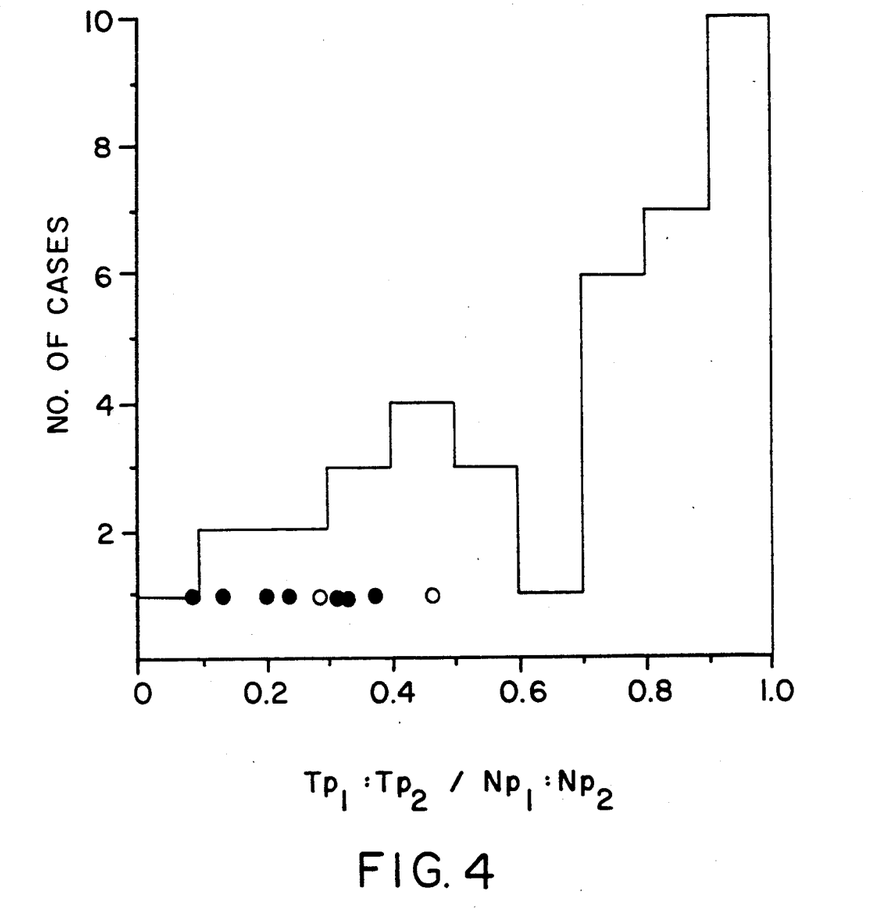
FIG. 4—Densitometric Scanning of Autoradiographs with Normal and Tumour DNA hybridised with λMS8

In order to obtain a more objective quantitative assessment of the allele ratios in the material given in Table 1, the autoradiographs for λMS8 were scanned densitometrically. From the scans, the ratios of the amounts of the two alleles in tumour material over those in the matched tissues could be estimated. For true allele loss, this derived ratio should be 0, but experimental error and normal tissue contaminating the tumour will lead to a distribution which should be bimodal. Preliminary results support this prediction and indicate nearly 40% (15 out of 39 cases scanned) have tumour/normal ratios in the lower part of this distribution, FIG. 4. This suggests that a more careful assessment of allele loss might lead to a higher estimate of the proportion of tumours which have lost a chromosome 5 allele. Those tumours showing allele loss which was easily detected by eye on the autoradiographs are indicated by circles in FIG. 4.

To determine whether the loss of alleles on chromosome 5 is specific and not simply a reflection of random loss, polymorphic markers on 6 other chromosomes were tested, namely 7,8,11,12,13,17. These were chosen because changes in chromosomes 7,8,12 and 17 have been reported in colorectal tumours[16-19]. These tumours are difficult to karyotype and in general show gross rearrangements and aneuploidy with no very specific chromosomal changes. Chromosomes 13 and 11 were tested because of their roles of retinoblastoma and Wilm's tumours respectively. The results for these other markers are shown in table 2. In only one case was heterozygosity not maintained, and this involved one tumour out of 21 which showed the loss of an allele on chromosome 12. In addition, ten informative normal/tumour pairs associated with the inherited cancer syndrome MEN$_2$ showed no loss of alleles on chromosome 5 using probe λMS8 (C. Mathew, pers comm). Thus, the loss of alleles appears to e chromosome-specific and possibly specific to this tumour.

Figure 3B:
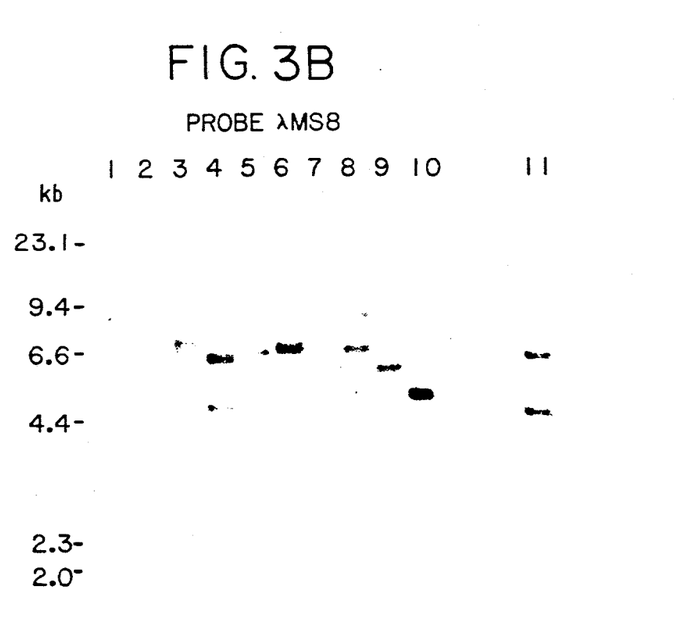

Ten established cell lines derived from sporadic colonic adenocarcinomas and from a polyp from an FAP case also were tested with probe λMS8. For the colorectal lines, matching normal tissue was not available, but since the predicted frequency of homozygotes is only 1 in 10, any increase beyond this could be significant. The data in FIG. 3B show that 4 of these ten lines are clearly homozygous nos. 5,7,9 and 10) and a fifth most probably so, (no. 6) strongly suggesting loss of a chromosome 5 as a significant genetic change in a remarkably high proportion of these tumours. The data on allele loss from cell lines are much clearer than for the fresh tumour material, as might be expected, since for the lines there is no problem of contamination by normal tissue. The Chi square

TABLE 2

| | Heterozygosity in colorectal carcinomas with chromosome-specific probes | | | |
|---|---|---|---|---|
| Chromosome | Probe (Enz. detecting RFLP) | No. of patients tested | No. of heterozygotes normal | No. of heterozygotes tumour | Ref. |
| 7 | D7S8 (MspI) | 17 | 9 | 9 | 21 |
|   | pλg3 (HinfI) | 9 | 9 | 9 | 13 |
| 8 | D8S8 (Taq I) | 33 | 14 | 14 | 22 |
| 11 | D11S16 (MspI) | 39 | 19 | 19 | 23 |
| 12 | pPstI (HindIII) | 31 | 17 | 16 | 24 |
|   | D12S2 (EcoRI) | 27 | 4 | 4 | 25 |
| 13 | D13S1 (MspI) | 26 | 13 | 13 | 26 |
|   | D13S2 (MspI) | 44 | 24 | 24 | 26 |
|   | D13S4 (MspI) | 37 | 22 | 22 | 26 |
| 17 | ERBA1 (PvuII) | 20 | 1 | 1 | 27 |
|   | D17S1 (MspI) | 41 | 15 | 15 | 28 |

Table 2

Tumour and normal DNA from colorectal cancer patients, hybridized with probes on chromosomes 7, 8, 11, 12, 13 and 17. Methods are as described in FIG. 1. DNA was digested with the enzymes indicated in parenthesis next to the probe name. Patients showing loss of chromosome 5 alleles (Table 1) were informative, but showed no loss for other probes as follows: patient 4—D7S8, D13S2; patient 5—D13S1, D17S1; patient 9—D11S16, D12S2, D17S1; patient 11—D13S4; patient 17—pλg3; patient 18—D13S2, D17S1; patient 19—D13S2, D13S4; patient 21—D12S2, D12S2; patient 28—D11S16; D13S2, D13S4, D17S1. ($X^2$) is 9 for the difference between 5/10 and the control λMS8 homozygote frequency of 5/60 and this is highly significant with pz0.35.

One of the cell lines showing λMS8 allele loss, PC/JW[19] was derived from a carcinoma from an FAP patient, which is of course consistent with the mapping of the FAP gene to chromosome 5. However, now that FAP patients are treated removal of the colon at a relatively early age to prevent cancers developing, it is not easy to obtain colorectal tumour material from FAP patients. We have, therefore, not yet been able to extend our observations to a larger number of familial cases of colorectal tumours. The cell line PC/AA[19], derived from a polyp, did not show loss of an λMS8 allele. This is consistent with tests, using λMS8 of premalignant polyps from 11 FAP patients, which showed no loss of heterozygosity in any case. The recessive change on chromosome 5 is, thus, secondary to the initial development of a polyp (see Example 1 for further discussion).

The overall data clearly show that a relatively high proportion of sporadic colorectal carcinomas loose all or part of one chromosome 5, presumably because loss of the FAP gene function favours tumour progression. The fact that λMS8 which is near the tip of 5q, demonstrated this loss, together with the comparatively common concomitant loss of an allele of the L1.4 locus, suggests that whole chromosome loss by non-disjunction, presumably following an initial mutation on one of the two chromosomes 5, is the commonest mechanism for becoming recessive, as has been found, for example, for retinoblastoma[2]. It would be expected, that this loss would be accompanied by reduplication since monosomy is likely to be disadvantageous for the growth of any cell, and non-disjunction is a relatively common event. Preliminary karyotyping of several cell lines supports this (data not shown). Even if technical developments increase the proportion of tumours with chromosome 5 allele loss to around 40%, there will still be a sizeable fraction of tumours in which no change on chromosome 5 is readily detectable. This could in part, of course, be due to relatively localised genetic mechanisms for producing the secondary change, such as point mutations, or small delections, or somatic crossing over. There is however, the further important likelihood that colorectal tumours are aetiologically heterogeneous with respect to the role of the FAP gene on chromosome 5. Those in which this activity is lost may represent a particular sub-set of colorectal tumours and this may have important implications for diagnosis and treatment. The combined studies of this and the accompanying paper on the localisation of the FAP gene and its probable role in a relatively high proportion of colorectal carcinomas, uncovers for the first time an important recessive genetic effect in one of the commonest of all cancers.

REFERENCES DESCRIPTION AND EXAMPLE 2

1. Knudson, A. G. Jnr., Proc. Nat. Acad. Sci. U.S.A. 68, 820-823 (1971)
*2. E. K. et al Nature 305, 779-784 (1983)
  * In the description only these references have a suffix "a".
*3. Sparkes, R. S. et al Science 219 971-973 (1983)
  * In the description only these references have a suffix "a".
*4. Koufos A. et al Nature 309, 170-172 (1984)
  * In the description only these references have a suffix "a".
*5. Orkin S. H., Goldman, D. S. & Sallan, S. E. Nature 309, 172-174 (1984)
  * In the description only these references have a suffix "a".
*6. Reeve A. E. et al Nature 309, 174-176 (1984)
  * In the description only these references have a suffix "a".
*7. Fearon E. R., Vogelstein, B & Feinberg A. P. Nature 309, 176-178 (1984)
  * In the description only these references have a suffix "a".
*8. Seizinger B. R., Martuza R. L., & Gusealla J. F. Nature 322, 644-647 (1986)
  * In the description only these references have a suffix "a".
*9. Hansen, M. F. et al Proc. Nat. Acad. Sci. U.S.A. 82 6216-6220 (1985)
  * In the description only these references have a suffix "a".
*10. Koufos, A. et al Nature 316 330-334 (1985)
  * In the description only these references have a suffix "a".
11. Bulow, S. Danish Med. Bull. 34 1-15 (1987)
12. Herrera, L. et al Am. J. Med. Genet., 25 473-476 (1986)
13. Wong, Z. et al Ann. Hum. Genet., in press
14. Bodmer, W. F. et al Nature 328, 614-616 (1987)
15. Pearson, P. in Eighth International Workshop on Human Gene Mapping Cytogent and Cell Genet 40 (1985)
16. Becher, R., Gibar, Z and Sandberg, A. A. Cancer Genet. and Cytogenet. 8 329-332 (1983)
17. Levin, B. and Reichmann, A. Cancer Genet. and Cytogenet. 19 159-162 (1986)
18. Reichmann, A. Martin, P. and Levin, B. Int. J. Cancer 28 431-440 (1981)
19. Paraskeva, C. et al Int. J. Cancer 34 49-56 (1984)
20. Dukes, C. E., J. Pathol. Baceriol. 35 323-332 (1932)
21. Bartels, K-H et al Eighth International Workshop on Human Gene Mapping Cytogent and Cell Genet. 40 (1985)
22. Brennan, J. et al Nucl. Acid Res. 22 9224 (1986)
23. Feder, J. et al Am. J. Hum. Genet. 37 635-649 (1985)
24. Sykes, B. et al Disease Markers 1 141-146 (1983)
25. Balazs I et al Somat. Cell Mol. Genet. 10 385-397 (1984)
26. Cavenee, W. K. et al Am. J. Hum. Genet. 36 10-24 (1984)
27. Rider, S. H. et al Nucl. Acid Res. 15 863 (1987)
28. Baker, D. & White, R. Cytogenet and Cell Genet. 32 253 (1982)
29. Maniatis, T., Fritsch, E. F. & Sambrook J. Molecular cloning, a Laboratory Manual, Cold Spring Harbor Laboratory, New York (1982)
30. Southern, E. M. J. Mol Biol. 98, 503 (1975)
31. Feinberg, A. P. & Vogelstein B. Analyt. Biochem. 132 6-13 (1983)
32. Carrel, S., Cordat B & Merenda C., Cancer Research 36 3978-3984 (1976)
33. Jones, S. L., Pathology 14 405-408 (1982)
34. Drewinko, E., Romsdahl, M. M., Yang, L. Y., Ahearn, M. J., & Trujillo, J. M., Cancer Research 36 467-475 (1976)
35. Rutzky, L. P. & Siciliani, M. J. J. Nat. Cancer Inst. 68(1), 81-90 (1982)
36. Leibovitz, A., Cancer Res. 36 4562-4567 (1976)

We claim:

1. An isolated nucleic acid fragment capable of selectively hybridising with the human chromosomes 5 at the chromosomal region 5q20-q23 other than the probe C11p11.

2. An isolated double-stranded DNA fragment capable of selectively hybridising under high stringency conditions with the human chromosome 5 at the chromosomal region 5q20-q23 other than probe C11p11.

3. A fragment according to claim 1 capable of selectively hybridising at the chromosomal region 5q21-q22 locus.

4. A fragment according to claim 3 and capable of recognising alleles of 3.9 and 4.4 kb in a TaqI digest of human chromosomes 5.

5. A fragment according to claim 4, 3.6 kb in length.

6. A nucleic acid probe comprising a fragment according to claim 1 and having a detectable label bound thereto.

7. A probe according to claim 6 wherein the label is a radiolabel, a fluorescent label or an enzyme label.

8. A process for producing the probe C11p11 or a fragment according to claim 1 comprising digesting human chromosomal DNA to form a library, cloning the library and screening and selecting from the cloned library fragments capable of selectively hybridising at the 5q20-q23 region of human chromosome 5.

9. A process for presymptomatic screening of an individual for FAP comprising contacting a sample of DNA from the individual with the C11p11 or a probe according to claim 6 under hybridising conditions.

10. A process for pathological classification of colonic tumors and precancerous polyps comprising contacting DNA from support tissue sample with the probe C11p11 or a probe according to claim 6 under hybridising conditions.

11. A fragment according to claim 2 capable of selectively hybridising at the chromosomal region 5q21-q22 locus.

12. A nucleic acid probe comprising a fragment according to claim 2 and having a detectable label bound thereto.

13. A nucleic acid probe comprising a fragment according to claim 3 and having a detectable label bound thereto.

14. A nucleic acid probe comprising a fragment according to claim 4 and having a detectable label bound thereto.

15. A nucleic acid probe comprising a fragment according to claim 5 and having a detectable label bound thereto.

16. A process for producing the probe C11p11 or a fragment according to claim 2 comprising digesting human chromosomal DNA to form a library, cloning the library and screening and selecting from the cloned library fragments capable of selectively hybridising at the 5q20-q23 region of the human chromosome 5.

17. A process for producing the probe C11p11 or a fragment according to claim 3 comprising digesting human chromosomal DNA to form a library, cloning the library and screening and selecting from the cloned library fragments capable of selectively hybridising at the 5q20-q23 region of the human chromosome 5.

18. A process for producing the probe C11p11 or a fragment according to claim 4 comprising digesting human chromosomal DNA to form a library, cloning the library and screening and selecting from the cloned library fragments capable of selectively hybridising at the 5q20-q23 region of the human chromosome 5.

19. A process for producing the probe C11p11 or a fragment according to claim 5 comprising digesting human chromosomal DNA to form a library, cloning the library and screening and selecting from the cloned library fragments capable of selectively hybridising at the 5q20-q23 region of the human chromosome 5.

20. A process for presymptomatic screening of an individual for FAP comprising contacting a sample of DNA from the individual with the probe C11p11 or a probe according to claim 7 under hybridising conditions.

21. A process for pathological classification of colonic tumors and precancerous polyps comprising contacting DNA from suspect tissue sample with the probe C11p11 or a probe according to claim 7 under hybridising conditions.

* * * * *